(12) United States Patent
Kidd et al.

(10) Patent No.: US 9,606,091 B2
(45) Date of Patent: Mar. 28, 2017

(54) METHODS OF MODELING AND MONITORING LEACHING BEHAVIOR OF POLYCRYSTALLINE DIAMOND AND METHODS OF LEACHING POLYCRYSTALLINE DIAMOND

(71) Applicant: US SYNTHETIC CORPORATION, Orem, UT (US)

(72) Inventors: Julie Ann Kidd, North Ogden, UT (US); Michael A. Vail, Genola, UT (US)

(73) Assignee: US SYNTHETIC CORPORATION, Orem, UT (US)

( * ) Notice: Subject to any disclaimer, the term of this patent is extended or adjusted under 35 U.S.C. 154(b) by 501 days.

(21) Appl. No.: 14/011,471

(22) Filed: Aug. 27, 2013

(65) Prior Publication Data

US 2016/0327530 A1    Nov. 10, 2016

Related U.S. Application Data

(60) Provisional application No. 61/694,368, filed on Aug. 29, 2012.

(51) Int. Cl.
*G01N 33/00* (2006.01)
*B01J 3/06* (2006.01)
*G06F 19/00* (2011.01)

(52) U.S. Cl.
CPC .............. *G01N 33/00* (2013.01); *B01J 3/06* (2013.01); *G06F 19/70* (2013.01); *B01J 3/062* (2013.01); *B01J 2203/062* (2013.01); *B01J 2203/0655* (2013.01); *B01J 2203/0685* (2013.01)

(58) Field of Classification Search
None
See application file for complete search history.

(56) References Cited

U.S. PATENT DOCUMENTS

| | | | |
|---|---|---|---|
| 6,338,754 | B1 | 1/2002 | Cannon et al. |
| 7,558,369 | B1 * | 7/2009 | Mourik .................. G01B 15/02 378/54 |
| 7,866,418 | B2 | 1/2011 | Bertagnolli et al. |
| 8,236,074 | B1 | 8/2012 | Bertagnolli et al. |

(Continued)

OTHER PUBLICATIONS

U.S. Appl. No. 61/694,368, filed Aug. 29, 2012, Kidd et al.

*Primary Examiner* — Guinever S Gregorio
(74) *Attorney, Agent, or Firm* — Dorsey & Whitney LLP

(57) ABSTRACT

Embodiments of the invention relate to methods of modeling leaching behavior of a polycrystalline diamond ("PCD") material used in leached polycrystalline diamond compacts ("PDCs") and methods of monitoring leaching of a PCD material. In an embodiment, a method of modeling leaching behavior is disclosed. A PCD table is provided, which includes a plurality of bonded diamond grains defining a plurality of interstitial regions in which a metallic material is disposed. The PCD table is leached with a leaching agent to at least partially remove the metallic material from the PCD table. A leach depth of the PCD table is determined. A concentration of at least one constituent of the leaching agent is also determined. The leach depth is correlated with the concentration of the at least one metal to generate the model of leaching behavior.

26 Claims, 13 Drawing Sheets

(56) References Cited

U.S. PATENT DOCUMENTS

| | | | | |
|---|---|---|---|---|
| 2010/0294571 A1* | 11/2010 | Belnap | ............... | B01J 3/062 |
| | | | | 175/434 |
| 2012/0000136 A1* | 1/2012 | Sani | ............... | B22F 7/08 |
| | | | | 51/295 |
| 2012/0152064 A1* | 6/2012 | Ladi | ............... | C22B 3/44 |
| | | | | 75/743 |

* cited by examiner

METHODS OF MODELING AND MONITORING LEACHING BEHAVIOR OF POLYCRYSTALLINE DIAMOND AND METHODS OF LEACHING POLYCRYSTALLINE DIAMOND

CROSS-REFERENCE TO RELATED APPLICATIONS

This application claims priority to U.S. Provisional Application No. 61/694,368 filed on 29 Aug. 2012, the disclosure of which is incorporated herein, in its entirety, by this reference.

BACKGROUND

Wear-resistant, superabrasive compacts are utilized in a variety of mechanical applications. For example, polycrystalline diamond compacts ("PDCs") are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller cone drill bits and fixed cutter drill bits. A PDC cutting element typically includes a superabrasive diamond layer (also known as a diamond table). The diamond table is formed and bonded to a substrate using an ultra-high pressure, ultra-high temperature ("HPHT") process. The PDC cutting element may also be brazed directly into a preformed pocket, socket, or other receptacle formed in the bit body. The substrate may be often brazed or otherwise joined to an attachment member, such as a cylindrical backing. A rotary drill bit typically includes a number of PDC cutting elements affixed to the bit body. It is also known that a stud carrying the PDC may be used as a PDC cutting element when mounted to a bit body of a rotary drill bit by press-fitting, brazing, or otherwise securing the stud into a receptacle formed in the bit body.

Conventional PDCs are normally fabricated by placing a cemented carbide substrate into a container with a volume of diamond particles positioned adjacent to a surface of the cemented carbide substrate. A number of such cartridges may be loaded into an HPHT press. The substrate and volume of diamond particles are then processed under HPHT conditions in the presence of a catalyst material that causes the diamond particles to bond to one another to form a matrix of bonded diamond grains defining a polycrystalline diamond ("PCD") table. The catalyst material is often a metal-solvent catalyst, such as cobalt, nickel, iron, or alloys thereof that is used for promoting intergrowth of the diamond particles.

In one conventional approach for forming a PDC, a constituent of the cemented carbide substrate, such as cobalt from a cobalt-cemented tungsten carbide substrate, liquefies and sweeps from a region adjacent to the volume of diamond particles into interstitial regions between the diamond particles during the HPHT process. The cobalt acts as a metal-solvent catalyst to promote intergrowth between the diamond particles, which results in formation of bonded diamond grains.

The presence of the metal-solvent catalyst in the PCD table is believed to reduce the thermal stability of the PCD table at elevated temperatures. For example, the difference in thermal expansion coefficient between the diamond grains and the metal-solvent catalyst is believed to lead to chipping or cracking of the PCD table during drilling or cutting operations, which can degrade the mechanical properties of the PCD table or cause failure. Additionally, some of the diamond grains can undergo a chemical breakdown or back-conversion to graphite via interaction with the metal-solvent catalyst. At elevated high temperatures, portions of diamond grains may transform to carbon monoxide, carbon dioxide, graphite, or combinations thereof, thus, degrading the mechanical properties of the PDC. One conventional approach for improving the thermal stability of a PDC is to at least partially remove the metal-solvent catalyst from the PCD table of the PDC by acid leaching.

SUMMARY

Embodiments of the invention relate to methods of modeling leaching behavior of PCD used in PDCs and methods of monitoring leaching of PCD. Embodiments also relate to applications for such leached PDCs in rotary drill bits, bearing apparatuses, wire-drawing dies, machining equipment, and other articles and apparatuses.

In an embodiment, a method of modeling leaching behavior and/or leaching is disclosed. A PCD table is provided, which includes a plurality of bonded diamond grains defining a plurality of interstitial regions in which a metallic material is disposed. The PCD table is leached with a leaching agent to at least partially remove the metallic material from the PCD table. A leach depth of the PCD table is determined. A concentration of at least one constituent of the leaching agent is also measured. The leach depth is correlated with the concentration of the at least one metal. In an embodiment, the correlation may be used to generate a model of leaching behavior.

In an embodiment, a method of monitoring leaching is disclosed. A PCD table is leached in a leaching agent to at least partially remove metallic material from the PCD table. The PCD table includes a plurality of bonded diamond grains defining a plurality of interstitial regions in which the metallic material is disposed. A concentration of at least one constituent of the leaching agent is measured. A leach depth in the PCD table is predicted at least partially based on the concentration.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

Embodiments of the invention relate to methods of modeling leaching behavior of PCD used in PDCs and methods of monitoring leaching of PCD. Embodiments also relate to applications for such leached PDCs in rotary drill bits, bearing apparatuses, wire-drawing dies, machining equipment, and other articles and apparatuses.

I. Introduction to PDCs and Methods of Manufacture of PDCs

Figure 1:
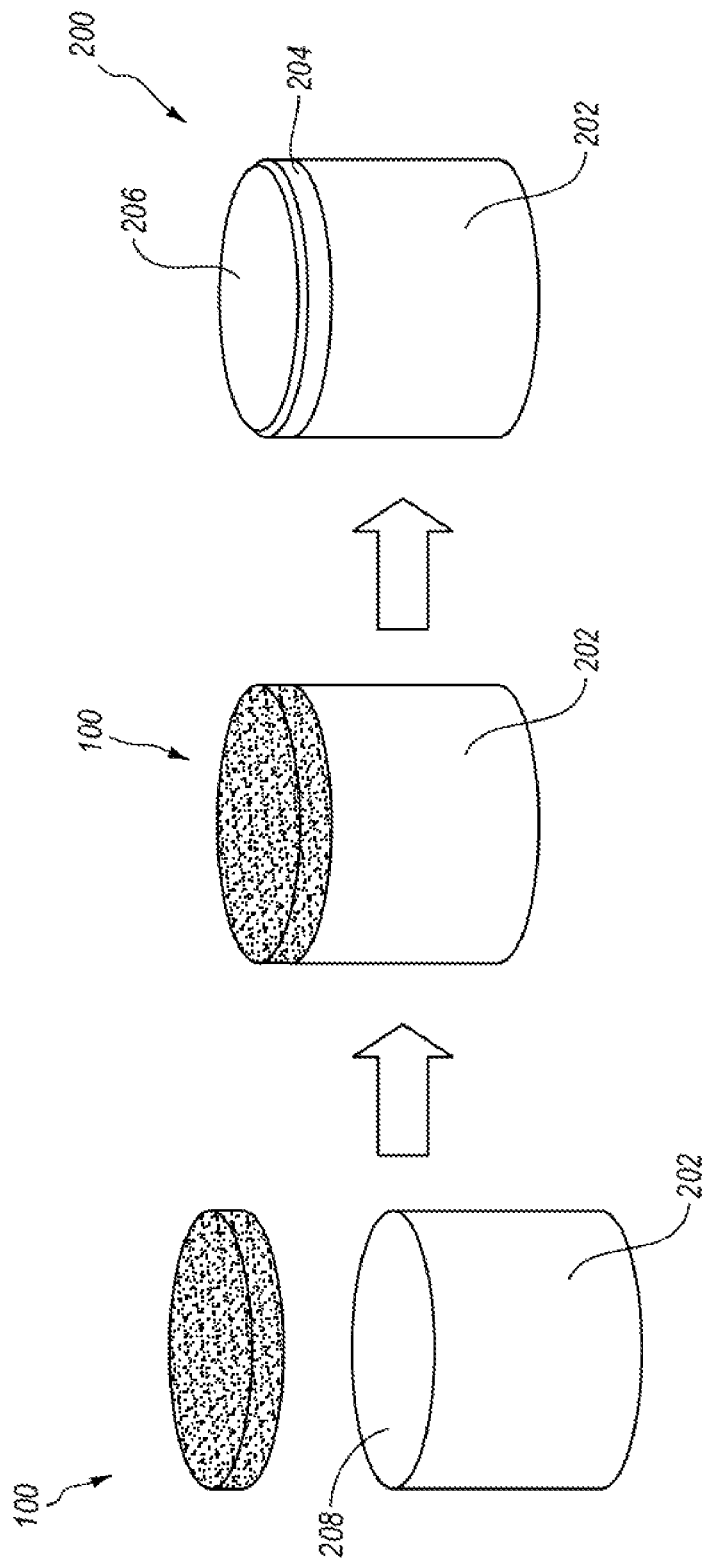
FIG. 1 is a schematic illustration of a method of fabricating a PDC according to an embodiment.

Various types of PDCs are described below, which may be employed in the different embodiments of methods of modeling leaching behavior and methods of monitoring leaching described below. FIG. 1 is a schematic illustration of an embodiment of a method for fabricating a PDC 200 that includes forming a PCD table 204 from a plurality of diamond particles 100. Referring to FIG. 1, the PCD table 204 may be fabricated by subjecting the plurality of diamond particles 100 (e.g., diamond particles having an average particle size between about 0.5 μm to about 150 μm) to an HPHT sintering process in the presence of a metal-solvent catalyst (i.e., a metallic material), such as cobalt, nickel, iron, or an alloy of any of the preceding metals to facilitate intergrowth between the diamond particles 100 and form the PCD table 204 comprising directly bonded-together diamond grains (e.g., exhibiting $sp^3$ bonding) defining interstitial regions with the metal-solvent catalyst disposed within at least a portion of the interstitial regions. In the illustrated embodiment, the PCD table 204 is formed by sintering the diamond particles 100 on a substrate 202, which may be a cobalt-cemented tungsten carbide substrate from which cobalt or a cobalt alloy infiltrates into the diamond particles 100. For example, the substrate 202 may comprise a cemented carbide material, such as a cobalt-cemented tungsten carbide material or another suitable material. For example, nickel, iron, and alloys thereof are other catalysts that may form part of the substrate 202. Other materials for the substrate 202 include, without limitation, cemented carbides including titanium carbide, niobium carbide, tantalum carbide, vanadium carbide, or combinations of any of the preceding carbides cemented with iron, nickel, cobalt, or alloys thereof. However, in other embodiments, the substrate 202 may be replaced or supplemented with a metal-solvent catalyst disc and/or catalyst particles may be mixed with the diamond particles 100.

The diamond particle size distribution of the plurality of diamond particles 100 may exhibit a single mode, or a bimodal or greater grain size distribution. In an embodiment, the diamond particles 100 may comprise a relatively larger size and at least one relatively smaller size. As used herein, the phrases "relatively larger" and "relatively smaller" refer to particle sizes (by any suitable method) that differ by at least a factor of two (e.g., 30 μm and 15 μm). According to various embodiments, the diamond particles 100 may include a portion exhibiting a relatively larger average particle size (e.g., 50 μm, 40 μm, 30 μm, 20 μm, 15 μm, 12 μm, 10 μm, 8 μm) and another portion exhibiting at least one relatively smaller average particle size (e.g., 6 μm, 5 μm, 4 μm, 3 μm, 2 μm, 1 μm, 0.5 μm, less than 0.5 μm, 0.1 μm, less than 0.1 μm). In an embodiment, the diamond particles 100 may include a portion exhibiting a relatively larger average particle size between about 10 μm and about 40 μm and another portion exhibiting a relatively smaller average particle size between about 1 μm and 4 μm. In some embodiments, the diamond particles 100 may comprise three or more different average particle sizes (e.g., one relatively larger average particle size and two or more relatively smaller average particle sizes), without limitation.

In an embodiment, the PCD table 204 may have a layered structure. For example, layered regions of diamond particles having a coarse average diamond particle size in a layer adjacent to the substrate 202 as compared to a layer having a fine average diamond particle size positioned near an upper surface 206 may provide for mitigating related high residual tensile stresses to thereby provide for secure bonding of the PCD table to the substrate. In an embodiment, the PCD table 204 may have two layers including diamond grains, two or more layers including diamond grains, or more than three layers including diamond grains may be employed. In an embodiment, each layer may have a progressively smaller average diamond particle size with distance away from the substrate 202.

The plurality of diamond particles 100 and substrate 202 may be subjected to an HPHT process to form the PDC 200. In such an embodiment, the PCD table 204 so-formed may include tungsten and/or tungsten carbide that is swept in with a metal-solvent catalyst (i.e., a metallic material) from the substrate 202. For example, some tungsten and/or tungsten carbide from the substrate 202 may be dissolved or otherwise transferred by the liquefied catalyst (e.g., cobalt from a cobalt-cemented tungsten carbide substrate) of the substrate 202 that sweeps into the diamond particles 100.

In order to efficiently sinter the plurality of diamond particles 100, the plurality of diamond particles 100 and substrate 202 may be enclosed in a pressure transmitting medium, such as a refractory metal can, graphite structure, pyrophyllite, combinations thereof, or other suitable pressure transmitting structure to form a cell assembly. Examples of suitable gasket materials and cell structures for use in manufacturing PCD are disclosed in U.S. Pat. Nos. 6,338,754 and 8,236,074, each of which is incorporated herein, in its entirety, by this reference. Another example of a suitable pressure transmitting material is pyrophyllite, which is commercially available from Wonderstone Ltd. of South Africa. The cell assembly, including the pressure transmitting medium and diamond particles 100 and substrate 202 therein, may be subjected to an HPHT process using an ultra-high pressure press (e.g., a cubic press) at a temperature of at least about 1000° C. (e.g., about 1100° C.

to about 2200° C., or about 1200° C. to about 1450° C.) and a pressure in the pressure transmitting medium of at least about 5 GPa (e.g., at least about 7.5 GPa, about 7.5 GPa to about 15 GPa, about 9 GPa to about 12 GPa, or about 10 GPa to about 12.5 GPa) for a time sufficient to sinter the diamond particles 100 together in the presence of the metal-solvent catalyst and form the PCD table 204 comprising bonded diamond grains defining interstitial regions occupied by the metal-solvent catalyst. For example, the pressure in the pressure transmitting medium employed in the HPHT process may be at least about 8.0 GPa, at least about 9.0 GPa, at least about 10.0 GPa, at least about 11.0 GPa, at least about 12.0 GPa, or at least about 14 GPa.

The pressure values employed in the HPHT processes disclosed herein refer to the pressure in the pressure transmitting medium at room temperature (e.g., about 25° C.) with application of pressure using an ultra-high pressure press and not the pressure applied to the exterior of the cell assembly. The actual pressure in the pressure transmitting medium at sintering temperature may be higher or lower. Additional details about methods of manufacturing the PDC 200 and properties of the PCD table 204 may be found in U.S. Pat. No. 7,866,418, which is incorporated herein, in its entirety, by this reference.

Figure 2A:
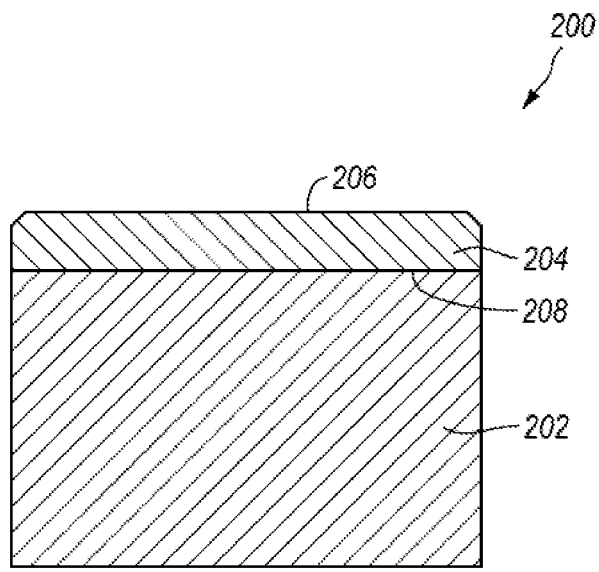
FIG. 2A is a cross sectional view of the PDC shown in FIG. 1.

FIG. 2A is a cross-sectional view of the PDC 200 formed by the method shown in FIG. 1. The PDC 200 so-formed includes the PCD table 204 that is integrally formed with the substrate 202 and bonded to an interfacial surface 208 of the substrate 202. If the substrate 202 includes a metal-solvent catalyst, the metal-solvent catalyst may liquefy and infiltrate the plurality of diamond particles 100 to promote growth between adjacent diamond particles of the plurality of diamond particles 100 to form the PCD table 204 comprised of a body of bonded diamond grains having the infiltrated metal-solvent catalyst interstitially disposed between bonded diamond grains. For example, if the substrate 202 is a cobalt-cemented tungsten carbide substrate, cobalt from the substrate 202 may be liquefied and infiltrate the mass of diamond particles 100 to catalyze formation of the PCD table 204.

In other embodiments, a PCD table according to an embodiment may be separately formed using an HPHT sintering process (e.g., subsequently separated from a first substrate 202, or formed without a substrate) and subsequently bonded to the interfacial surface 208 of the substrate 202 by brazing, using a separate HPHT bonding process, or any other suitable joining technique, without limitation. In other embodiments, a PCD table (e.g., the PCD table 204 or a free-standing PCD table) may be formed using an HPHT sintering process as described above, subsequently separated from the substrate 202, subsequently leached to at least partially or substantially completely remove the metal-solvent catalyst used in the fabrication thereof, and infiltrated with a metallic infiltrant (i.e., a metallic material) from another substrate 202 to bond the at least partially leached PCD table to the interfacial surface 208 of the substrate 202. For example, the metallic infiltrant may be cobalt from a cobalt-cemented tungsten carbide substrate.

Figure 2B:
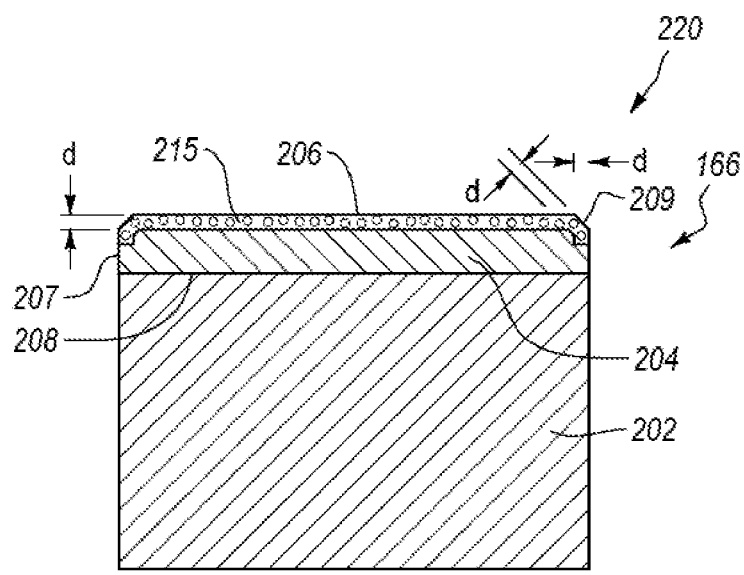
FIG. 2B is a cross-sectional view of the PDC shown in FIG. 1 after leaching the PCD table of the PDC to form a leached region according to an embodiment.

The PCD table 204 may be leached to deplete the metallic material (i.e., the metal-solvent catalyst and/or metallic infiltrant) therefrom that is used to occupy the interstitial regions between the bonded diamond grains of the PCD table 204 using an acid leaching process. The leaching may be performed in a suitable leaching agent, such as an acid of aqua regia, nitric acid, hydrofluoric acid, hydrochloric acid, or combinations thereof. Referring to FIG. 2B, the metallic material may be acid leached to a selected depth "d" measured from at least one of an upper surface 206, at least one lateral surface 207, or a chamfer 209 extending therebetween to form a leached region 215 that is depleted of the metallic material and a leached PDC 220. For example, the leached region 215 may generally contour the upper surface 206, the chamfer 209, and the at least one lateral surface 207 of the PCD table 204. The leached region 215 may extend along a selected length of the at least one lateral surface 207. In various embodiments, the selected depth "d" is less than about 1000 μm, about 50 μm to about 100 μm, about 200 μm to about 350 μm, about 400 μm to about 600 μm, about 600 μm to about 800 μm, or about 10 μm to about 500 μm. As a result of the metallic material being depleted from the PCD table 204, the PCD table 204 is relatively more thermally stable than conventional PCD tables.

A residual amount of the metallic material may also be present in the leached region 215 even after leaching. For example, the metallic material may be present in the leached region 215 in an amount of about 0.8 weight % to about 1.50 weight %, or about 0.9 weight % to about 1.2 weight % of the leached region 215.

II. Embodiments of Methods of Modeling Leaching Behavior

As leaching has been linked with increasing a thermal stability of PCD, an improved understanding of leaching behavior of PCD bodies during the leaching process, such as a kinetic model of such behavior, may aid in designing more thermally-stable PCD bodies and PDCs.

Figure 3A:
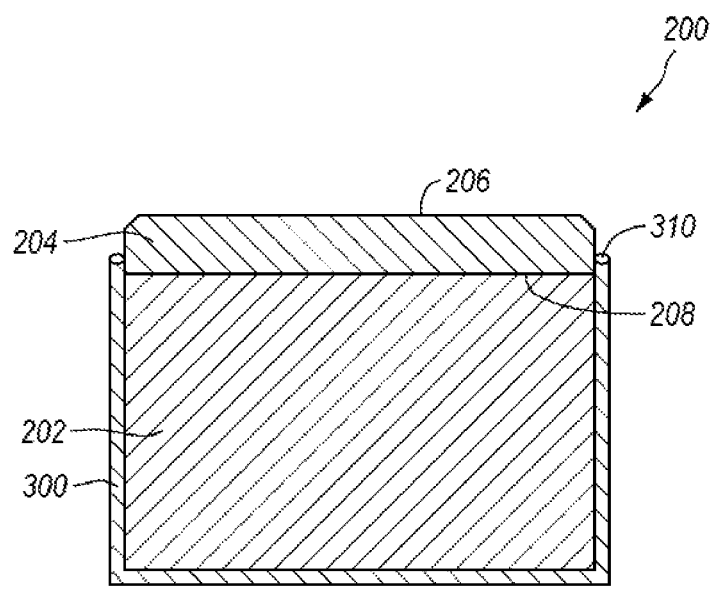
FIGS. 3A-3E are cross-sectional views that illustrate an embodiment of a method of leaching a PCD table to at least partially remove a metallic material therefrom, while acquiring data by monitoring a leach depth of the PCD table and a concentration of at least one constituent of a leaching agent used to leach the PCD table for modeling leaching behavior.

FIGS. 3A-3E illustrate an embodiment of a method of leaching a PCD table to at least partially remove a metallic material therefrom, while acquiring data by monitoring a leach depth of the PCD table and a concentration of metal-solvent catalyst (e.g., cobalt, iron, or nickel) or other constituent within a leaching agent used to leach the PCD table for modeling leaching behavior. FIG. 3A is a cross-sectional view of the PDC 200 (shown in FIG. 2A) that is at least partially surrounded by a protective layer 300 according to at least one embodiment. As shown in FIG. 3A, at least a portion of PDC 200, including substrate 202, may be surrounded by the protective layer 300 including a protective seal region 310. According to an embodiment, the protective layer 300 may comprise an inert cup. The combination of the protective layer 300 and the protective seal region 310 may prevent the leaching agent from chemically damaging certain portions of the PDC 200, such as the substrate 202 and/or a selected portion of PCD table 204, during leaching. The protective layer 300 and protective seal region 310 may be selectively formed, installed, positioned, or combinations thereof over the substrate 202 and a selected portion of PCD table 204 in varied patterns, designs, or as otherwise desired, without limitation. Such a configuration may provide selective leaching of the PCD table 204, which may be beneficial.

Figure 3B:
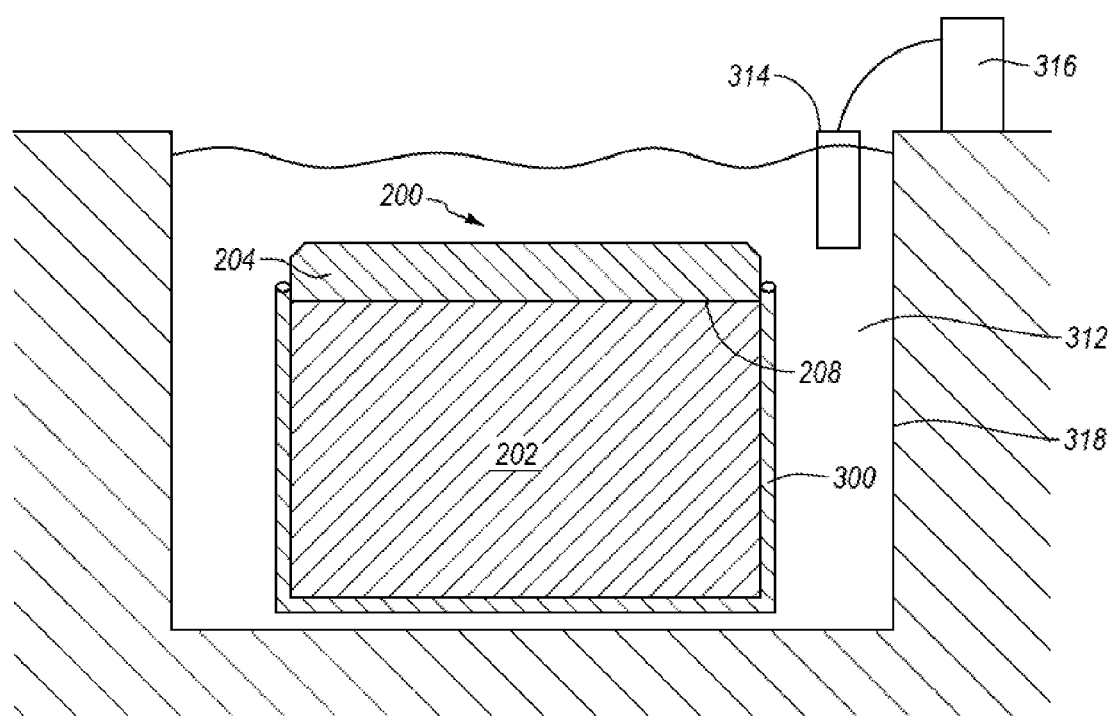

FIG. 3B depicts a method of monitoring the leaching process of the PCD table 204. The PDC 200 may be disposed in a receptacle 318 including a leaching agent 312 contained therein, such as any of the aforementioned leaching acids. A sensor 314 may be disposed in the leaching agent 312, which communicates with an analysis device 316 (e.g., a spectrometer or other analysis device) that monitors a concentration of at least one metal of the metallic material in the leaching agent 312 that is removed from the PCD table 204 during the leaching process. For example, the at least one metal may be cobalt, nickel, iron, or combinations thereof that was used in the sintering of the PCD table 204 or infiltrated into the PCD table 204. As another example, other constituents that may be monitored include, but are not limited to, niobium, tungsten, molybdenum, silver, aluminum, boron, barium, beryllium, calcium, cadmium, chromium, copper, lithium, potassium, magnesium, manganese, sodium, lead, silicon, titanium, vanadium, zinc, carbonates (e.g., barium carbonate, calcium carbonate, magnesium carbonate, or lithium carbonate), carbon, oxygen or combinations thereof. In the illustrated embodiment, the analysis device 316 may be configured to in situ monitor the leaching process either periodically or substantially continuously in order to record a leaching period (e.g., time elapsed) and to quantify a concentration of the at least one metal within the leaching agent solution 312. Instead of in situ monitoring of the concentration, in an embodiment, the monitoring may be performed by periodically or substantially continuously removing a sample of the leaching agent 312 (e.g., via a syringe (not shown) or any other suitable method/apparatus) followed by determining (e.g., measuring) the concentration of the sample.

As discussed above, analysis of the leaching agent 312 during the leaching process may be performed using the analysis device 316. For example, the analysis device 316 may be an inductively coupled plasma ("ICP") spectrometer, an inductively coupled plasma atomic mass spectrometer ("ICP/MS"), an inductively coupled plasma emission spectrometer ("ICP/AES"), a pH meter, an infrared spectrophotometer, or another suitable analysis device. ICP/MS is capable of detecting metals and several non-metals in the leaching agent solution 312 at concentrations as low as one part in $10^{12}$ (parts per trillion). This is achieved by sampling the leaching agent 312 (e.g., ionizing the leaching agent 312 with inductively coupled plasma or any other suitable method) and then using an analysis device (e.g., a mass spectrometer) to quantify its composition or properties. For example, ICP/AES, also known as inductively coupled plasma optical emission spectroscopy ("ICP-OES"), is also an analytical technique that may be used for the detection of trace metals from the metallic material within the liquid leaching agent solution 312. ICP/AES is a type of emission spectroscopy that uses the inductively coupled plasma to produce excited atoms and ions within the leaching agent solution 312 that emit electromagnetic radiation at wavelengths characteristic of a particular metal or element. The intensity of this emission is indicative of the concentration of the at least one metal of the metallic material within the leaching agent 312.

In an embodiment, the leaching agent 312 may be analyzed using a pH meter. A pH meter is an instrument configured to measure the acidity or alkalinity (e.g., the pH) of a liquid such as the leaching agent 312. A pH meter generally includes a measuring probe (e.g., a glass electrode) connected to an electronic meter that measures and displays the pH reading. The measuring probe measures pH as the concentration of the hydrogen cations (e.g., $H^+$ cations, or hydronium cations, $H_3O^+$) surrounding a thin-walled glass sensor at its tip. The measuring probe produces a small voltage that is measured and displayed as pH units by the instrument. For example, a pH reading of about 7.0 reflects a neutral leaching agent 312 with a pH reading less than about 7.0 reflecting an acidic leaching agent 312 and a reading greater than about 7.0 reflecting a basic leaching agent 312.

In an embodiment, the leaching agent 312 may be analyzed using an infrared spectrophotometer. A spectrophotometer may provide a quantitative measurement of the reflection or transmission properties of the leaching agent 312 as a function of wavelength. Spectrophotometry encompasses visible light, near-ultraviolet, and near-infrared light. An infrared spectrophotometer uses infrared light. The spectrophotometer is an instrument that can measure intensity as a function of the light source wavelength. A spectrophotometer may be used to determine what substances are present in a solution and quantitatively measure of the concentration of those substances. For example, a spectrophotometer may be used to determine a quantity of a particular metal or element within the leaching agent 312.

In an embodiment, the concentration of the at least one metal of the metallic material or other constituent within the leaching agent 312 may be measured using the analysis device 316. For example, the concentration of the at least one metal of the metallic material in the leaching agent 312 may be measured manually or automatically using the analysis device 316 at least once about every half hour for about 72 hours, at least once about every hour for about 48 hours, at least once about every 2 hours for about 24 hours, at least once about every 3 hours for about 24 hours, at least once every about 4 hours for about 24 hours, at least once about every 5 hours for about 24 hours, or at least once every about 6 hours for up to about 72 hours.

In an embodiment, the concentration of the at least one metal of the metallic material and/or other constituent in the leaching agent 312 may be monitored periodically or continuously. For example, the concentration of the at least one metal of the metallic material and/or other constituent in the leaching agent 312 may be monitored over a period of up to about 4 days, up to about 7 days, up to about 10 days, for greater than about a week, for greater than about 10 days, or other suitable period.

The analysis of the leaching agent 312 using methods discussed above during the leaching process will provide concentration data about the at least one metal within the leaching agent 312.

In an embodiment the analysis of the leaching agent 312 using any of the methods described herein may be used to characterize both the leachant and the leachate to determine the status of the leach process. For example, ICP methods described herein may be used to determine whether the leaching agent 312 is saturated with metal of the metallic material from the PCD table 204 indicating that the leaching agent 312 should be changed or that the leaching process is complete.

Figure 3C:
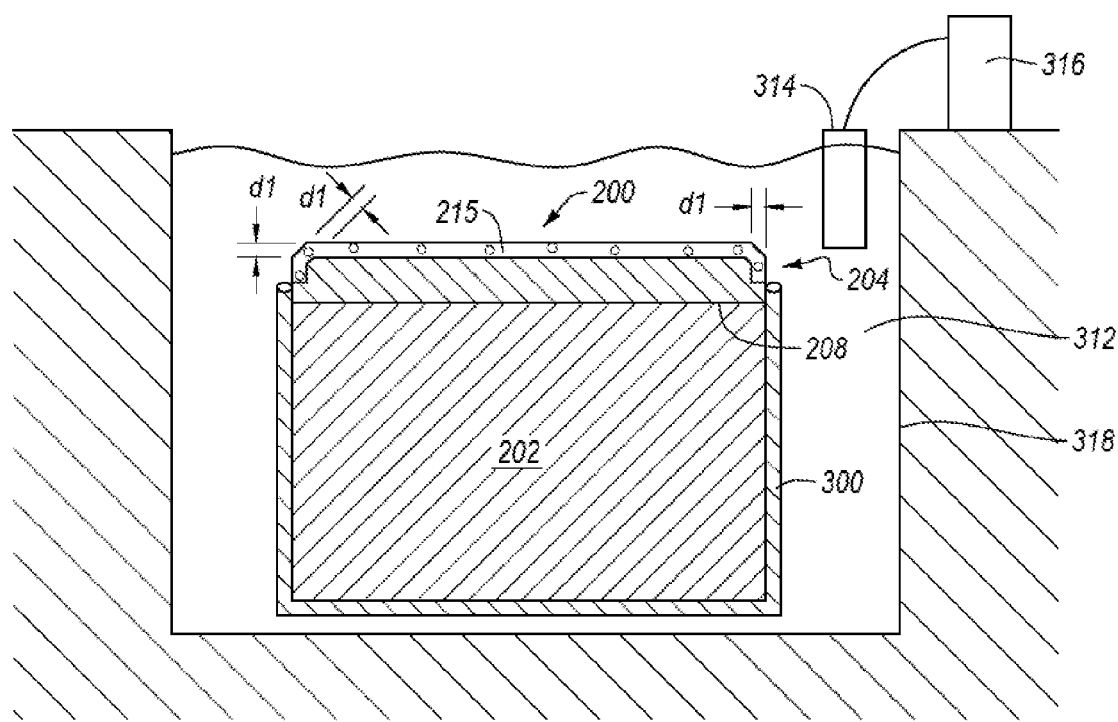
Figure 3D:
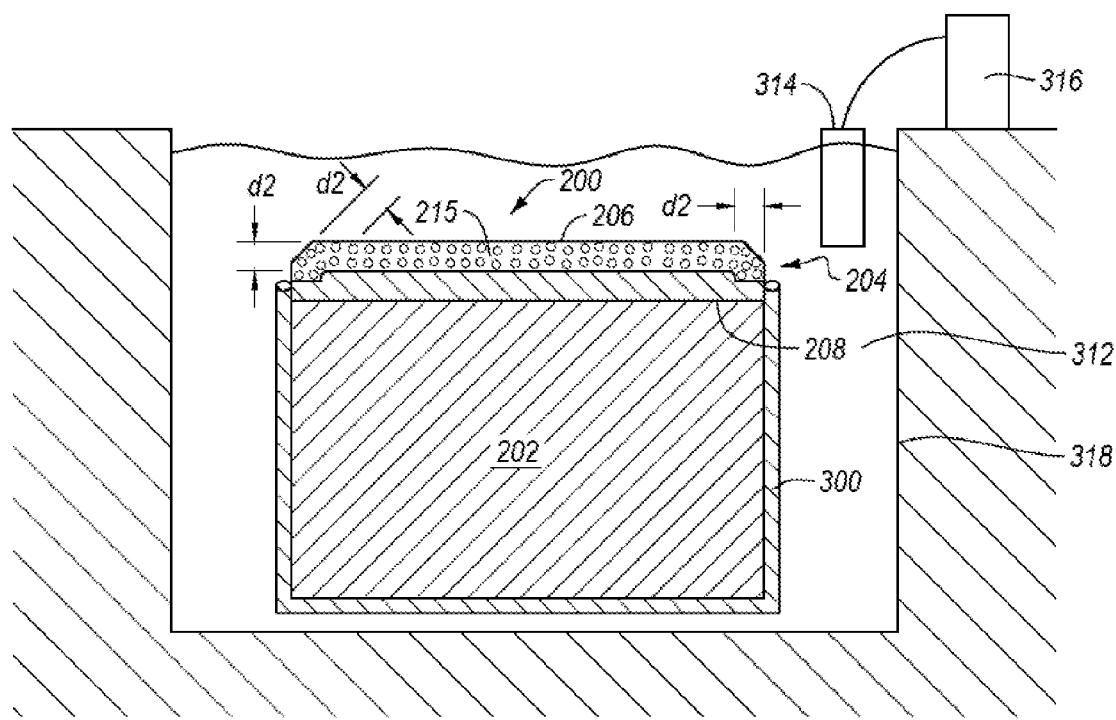

The leach depth "d1" of the PCD table 204 shown in FIG. 3C, or "d2" of the PCD table 204 shown in FIG. 3D may also be analyzed and determined/measured periodically using non-destructive or destructive techniques (e.g., beta-backscatter, x-ray fluorescence spectroscopy, x-ray radiography, exposure to radiation, cross-sectioning, preparing photomicrographs, or another suitable technique) The increasing leach depth of the leach treated PCD table 204 may be monitored during the leaching process by removing the PDC 200 periodically from the leaching agent 312 and measuring the leach depth "d" using any of the aforementioned non-destructive or destructive testing methods. For example, the leach depth "d1" or "d2" of the PCD table 204 may be determined periodically at least once every about 1 hour, 2 hours, 3 hours, or 4 hours for about 24 hours, or other selected time period. In an embodiment, the leach depth "d1" or "d2" of the PCD table 204 may be monitored over a period of up to about 7 days.

Figure 3E:
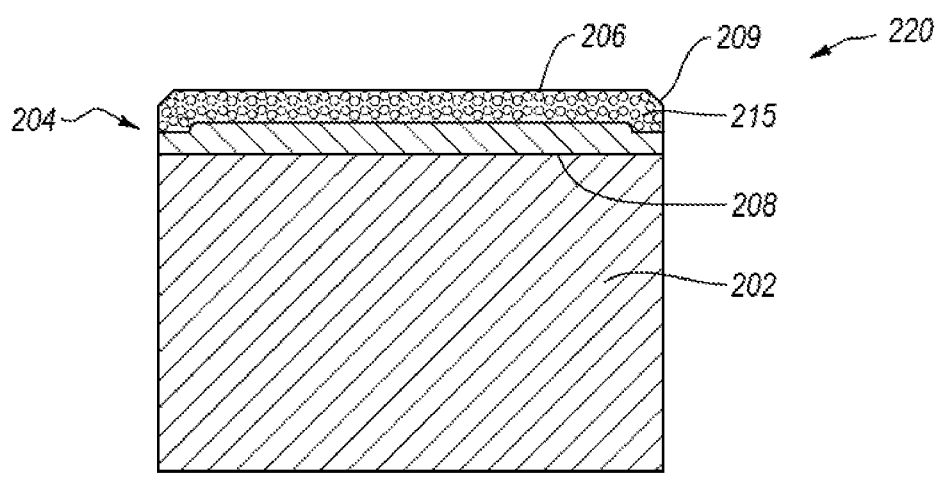

The analysis of the PCD table 204 using the above-mentioned methods during the leaching process provides data values for the leach depth "d1" or "d2" of the PCD table 204 shown in FIGS. 3C and 3D. For example, the leach depth "d1" or "d2" of the PCD table 204 may be less than about 1000 μm, about 50 μm to about 100 μm, about 200 μm to about 350 μm, about 400 μm to about 500 μm, about 600

μm to about 800 μm, or about 10 μm to about 500 μm. Referring to FIGS. 3C and 3D, the leached region 215, including the leach depths "d1" and "d2", respectively, is shown to progressively increase within the PCD table 204 with increasing temporal exposure to the leaching agent 312. Referring to FIG. 3E, following the leaching process, a PDC 220 exhibiting the leached region 215 so-formed may be removed from the receptacle 318 and the protective layer 300.

Analysis of the collected data from the leaching process of the PCD table 204 may be used for correlating the determined leach depth "d" and the corresponding measured concentration of the at least one metal from the metallic material and/or other constituent so removed to predetermined time intervals at which the measurements are made to generate a kinetic model of leaching behavior of the PCD table.

Figure 4:
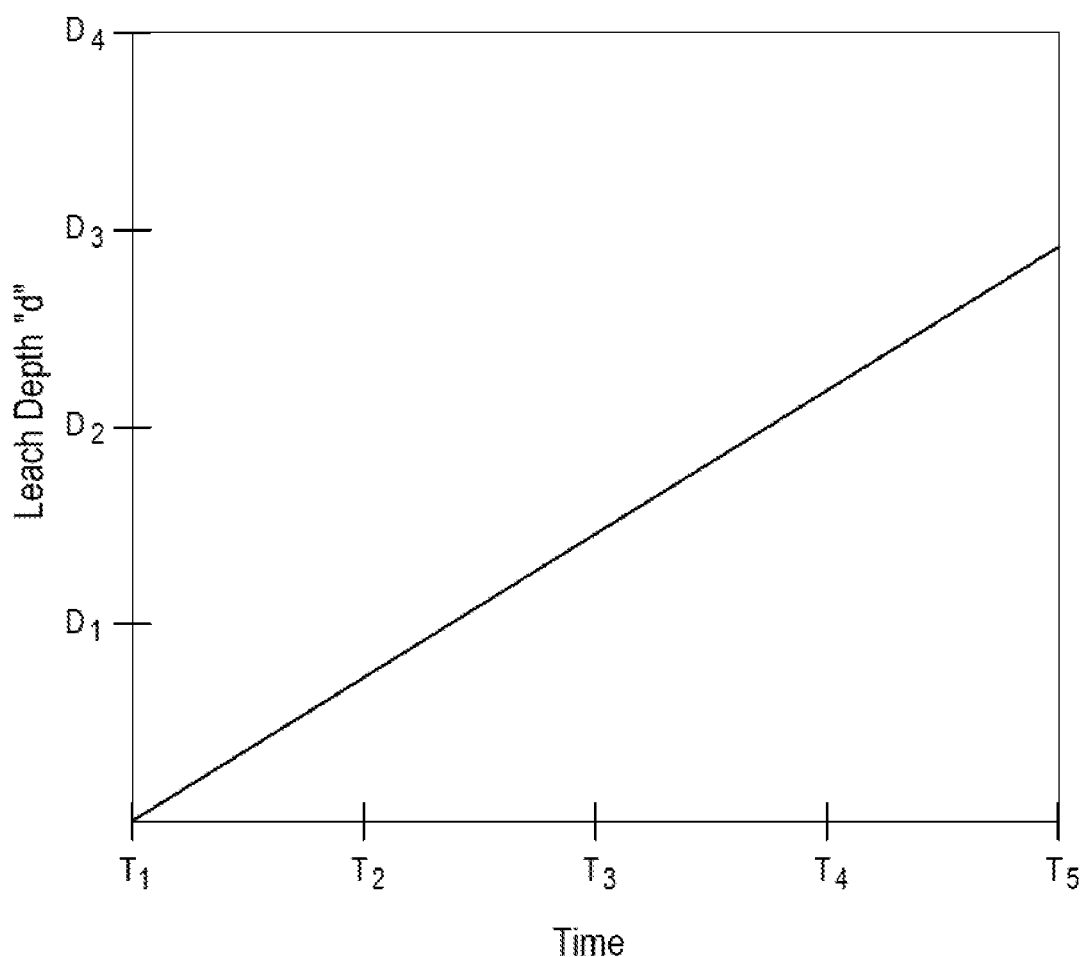
FIG. 4 is a graph of leach depth of a PCD table versus elapsed leach time during a leaching process according to an embodiment.

Following collection of the leach depth "d" and concentration data at the selected time intervals, the collected data may be analyzed. FIG. 4 is a graph that displays a generally linear relationship between the respective values of leach depth "d" and leach time elapsed during the leaching process according to an embodiment. For example, the data values for the leach depth "d" may be collected at selected time intervals. The so-collected data values for the leach depth "d" may be plotted versus the elapsed leach time ($T_1$, $T_2$, $T_3$, and $T_4$) to provide the graph shown in FIG. 4. As observed, the scatter plot of FIG. 4 provides a generally linear relationship between increased leach depth and increased leach time. In another embodiment, the slope of the line in the graph of leach depth versus leach time may vary from that shown in FIG. 4. For example, depending on whether additional leaching agent 312 is added or replaced during the leaching process, or whether the leaching process results in evaporation of the leaching agent 312, the slope of the line may increase or decrease.

Figure 5:
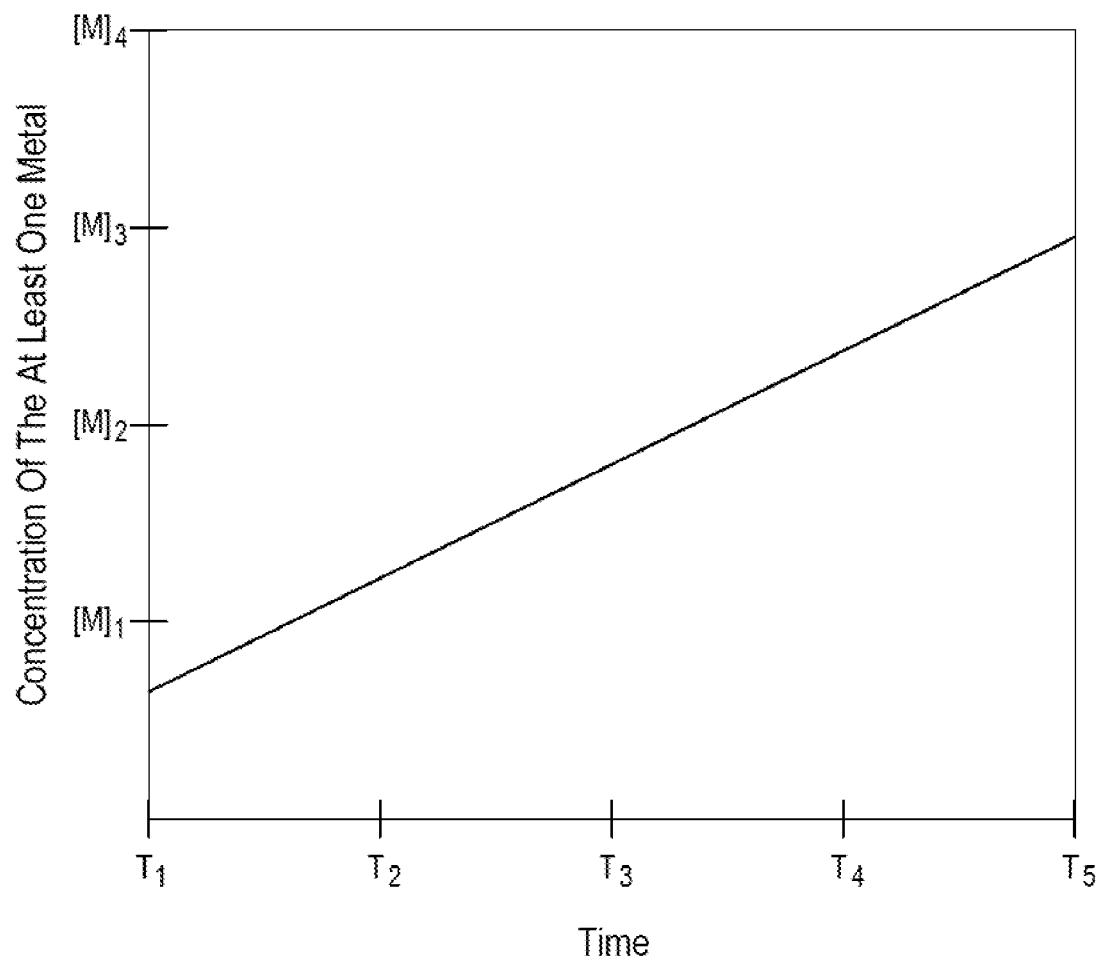
FIG. 5 is a graph of the concentration of at least one metal from a metallic material leached from a PCD table that is present in a leaching agent versus elapsed leach time during a leaching process according to an embodiment.

FIG. 5 is a graph that displays the generally linear relationship between the concentration of the at least one metal within the leaching agent 312 and the elapsed leach time during the leaching process according to an embodiment. For example, the concentration values may be collected during the leaching process at selected time intervals to generate the graph shown in FIG. 5. It may be observed in the graph shown in FIG. 5 that the concentration of the at least one metal values much like the leach depth values of FIG. 4, increase generally linearly as the leach time elapsed increases. In another embodiment, the slope of the line in the graph of concentration of the at least one metal versus leach time may vary from that shown in FIG. 5. For example, depending on whether additional leaching agent 312 is added or replaced during the leaching process, or whether the leaching process results in evaporation of the leaching agent 312, the slope of the line may increase or decrease.

As may be observed by comparing the results shown in FIGS. 4 and 5, the graphs show substantially similar behavior of the parameters of leach depth "d" and concentration of the at least one metal of the metallic material removed from the PCD table 204 as compared to leach time. The leaching behavior observed in both FIGS. 4 and 5 provides a kinetic model that may be used for correlating values of the monitored leach depth "d" to values of the monitored concentration of the at least one metal to form a model of leaching behavior according to an embodiment. It should be noted that the correlation may be performed computationally by at least one processor of a computing system. In some embodiments, the at least one processor may be incorporated into the analysis device 316, and the analysis device 316 may be programmed to output a graph illustrating the correlation of the monitored leach depth "d" to values of the monitored concentration of the at least one metal, such as shown in FIG. 6.

In other embodiments, the concentration of the at least one metal may be controlled. For example, additional leaching agent may be added and/or leaching agent with a certain concentration of the at least one metal may be removed, as desired or needed. Such a method may result in faster leaching, and may be automated.

In another embodiment, a change in the slope of the line shown in FIG. 4 may indicate the need to add additional leaching agent. For example, should the slope of FIG. 4 decrease from an initial value to a selected, lower value, new, additional leaching agent may be added and/or at least a portion of the leaching agent with a certain concentration may be added.

Figure 6:
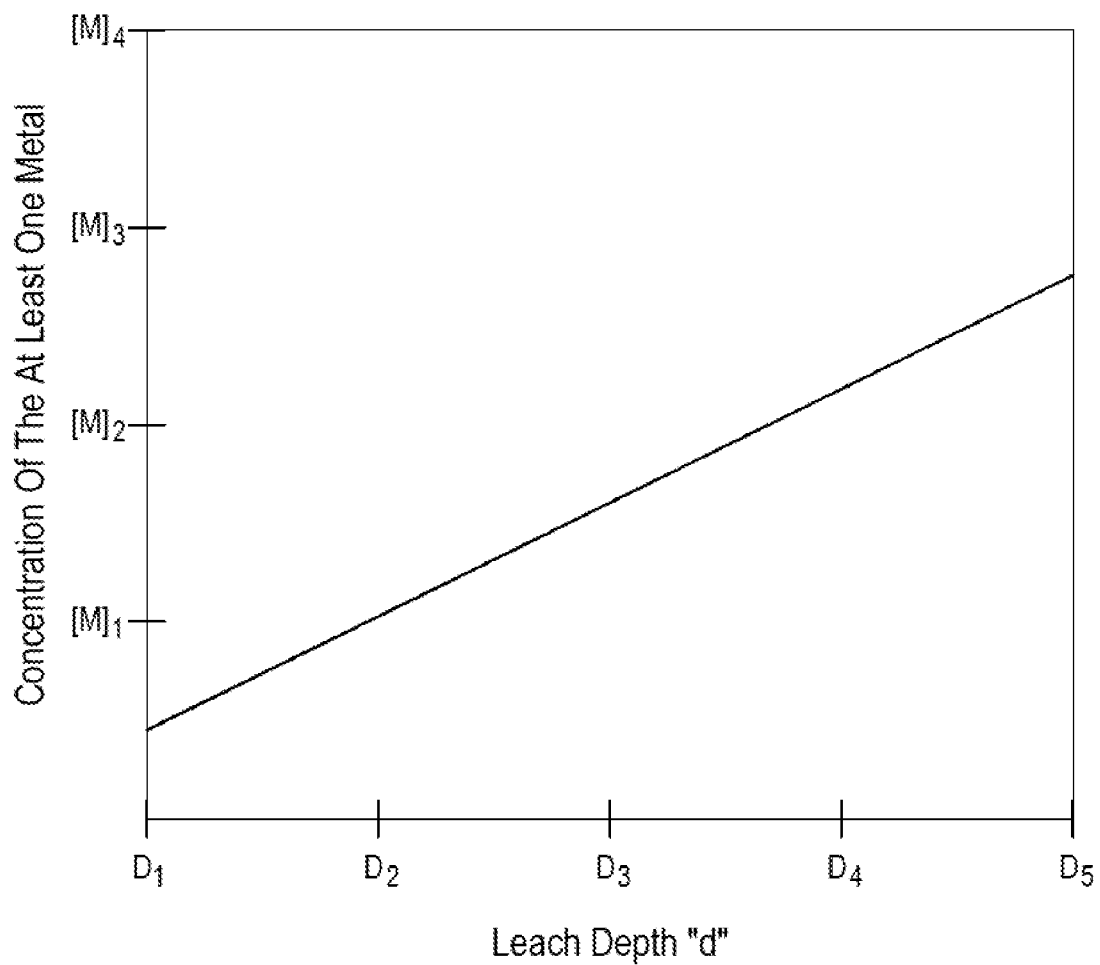
FIG. 6 is a graph of the concentration of at least one metal from a metallic material versus the leach depth according to an embodiment.

FIG. 6 is a graph that displays the generally linear correlation between the concentration of the at least one metal within the leaching agent 312 and the leach depth "d" according to an embodiment. This kinetic model shows a proportionality of metal concentration and leach depth behavior. The model of leaching behavior shown in FIG. 6 also provides for a more predictable design of leached PCD bodies, thereby allowing for more effective fabrication of thermally stable PCD bodies and PDCs. In another embodiment, the slope of the line in the graph may vary from that shown in FIG. 6. For example, depending on whether additional leaching agent 312 is added or replaced during the leaching process, or whether the leaching process results in evaporation of the leaching agent 312, the slope of the line may increase or decrease, or exhibit non-linear behavior.

In an embodiment, the model of leaching behavior may assist in engineering and fabricating PCD tables, such as PCD table 204 (as shown in FIGS. 2A and 3A-3E) with a targeted/desired leach depth "d". Values from the kinetic model for the metal concentration within the leaching agent 312 may be used to achieve the correlated desired leach depth, "d" of the PCD table. For example, the concentration of the at least one metal from the metallic leaching agent 312 may be monitored during a leaching process of the PCD table 204, and the PCD table 204 may be withdrawn from the leaching agent 312 at substantially the metal concentration value correlated to the desired leach depth "d" value, as predicted by the kinetic model. Such a fabrication procedure employing parameters determined by the kinetic model described herein may result in the predicted, successful fabrication of the PCD table 204 having substantially the targeted/desired leach depth "d".

In the case where the leaching agent is "refreshed" with new additional leaching agent, a cumulative amount of the at least one metal may be estimated and correlated to the leach depth. Thus, by estimating and/or calculating a cumulative amount of the at least one metal, a desired leach depth "d" may be attained through leaching.

III. Embodiments of Methods of Monitoring Leaching of a PCD Table

Embodiments of the invention also include methods of monitoring leaching a PCD table for leaching quality control. According to an embodiment, a method of monitoring leaching of a PCD table is disclosed. The methods may employ the model of leaching behavior generated from the plots shown in FIGS. 4-6. The model may be used to monitor, adjust, modify, or combinations thereof the leaching of metallic material from a PCD table of a PDC manufactured in the same or similar manner to that of the PDC 200 and the PDC 200 is used when describing the methods of monitoring leaching disclosed herein.

According to an embodiment, the PDC 200 may be masked and immersed in the leaching agent 312 to at least partially remove metallic material from the PCD table 204 as shown and previously described with respect to FIG. 3B. A concentration of at least one constituent or at least one metal from the metallic material within the leaching agent 312 may be determined. For example, the concentration may be determined in situ or ex situ using an ICP spectrometer, an ICP/MS, an ICP/AES, or another suitable chemical analysis device as previously described. The concentration may be compared to the model of leaching behavior of the PCD table 204 previously determined from the graphs shown in FIGS. 4-6 to determine a predicted leach depth "d" that corresponds to the concentration. That is, for each measured concentration, the model of leaching behavior provides a predicted leach depth "d."

In an embodiment, the kinetic model may be used to determine problems with the leaching process. As an example, if the concentration of the at least one metal from the metallic material within the leaching agent 312 determined indicates that the predicted leach depth "d" is far greater than expected after a given leaching time for achieving a target/desired leach depth, the leaching process may be terminated by removing the PDC 200 from the leaching agent. This may occur when there is some anomalous behavior in the leaching process, such as the strength of the leaching agent 312 being too strong and/or the PCD table 204 being different than the PCD used to calibrate the model. As another example, if the concentration of the at least one metal from the metallic material within the leaching agent 312 determined indicates that the predicted leach depth "d" is far less than it should be after a given leaching time for achieving a target/desired leach depth, the leaching process may be terminated by removing the PDC 200 from the leaching agent and adjusting the strength of the leaching agent 312. This may occur when there is some anomalous behavior in the leaching process, such as the strength of the leaching agent 312 being too weak.

Like the leaching agent strength discussed above, other working parameters, related to the leaching process may also be modified or adjusted during leaching in response to the monitoring of those respective parameters. For example, the temperature, the pressure, and/or the volume of acid of the leaching agent 312 may be adjusted or modified based on the acidic concentration, the concentration of the at least one metal, the monitored temperature and pressure, or the pH of the leaching agent 312.

IV. Applications for Leached PDCs

Figure 7:
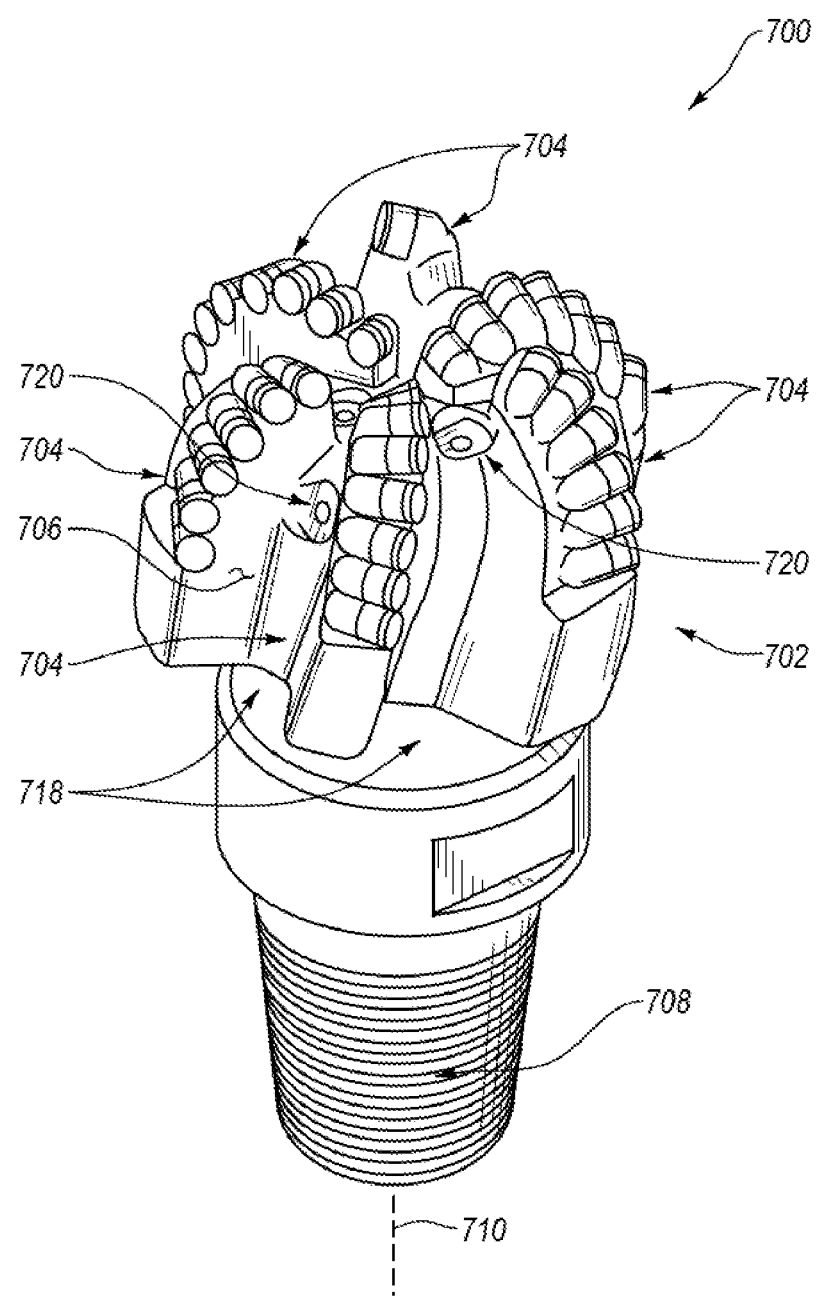
FIG. 7 is an isometric view of a rotary drill bit according to an embodiment that may employ one or more of the leached PDCs disclosed herein according to any of the embodiments disclosed herein.
Figure 8:
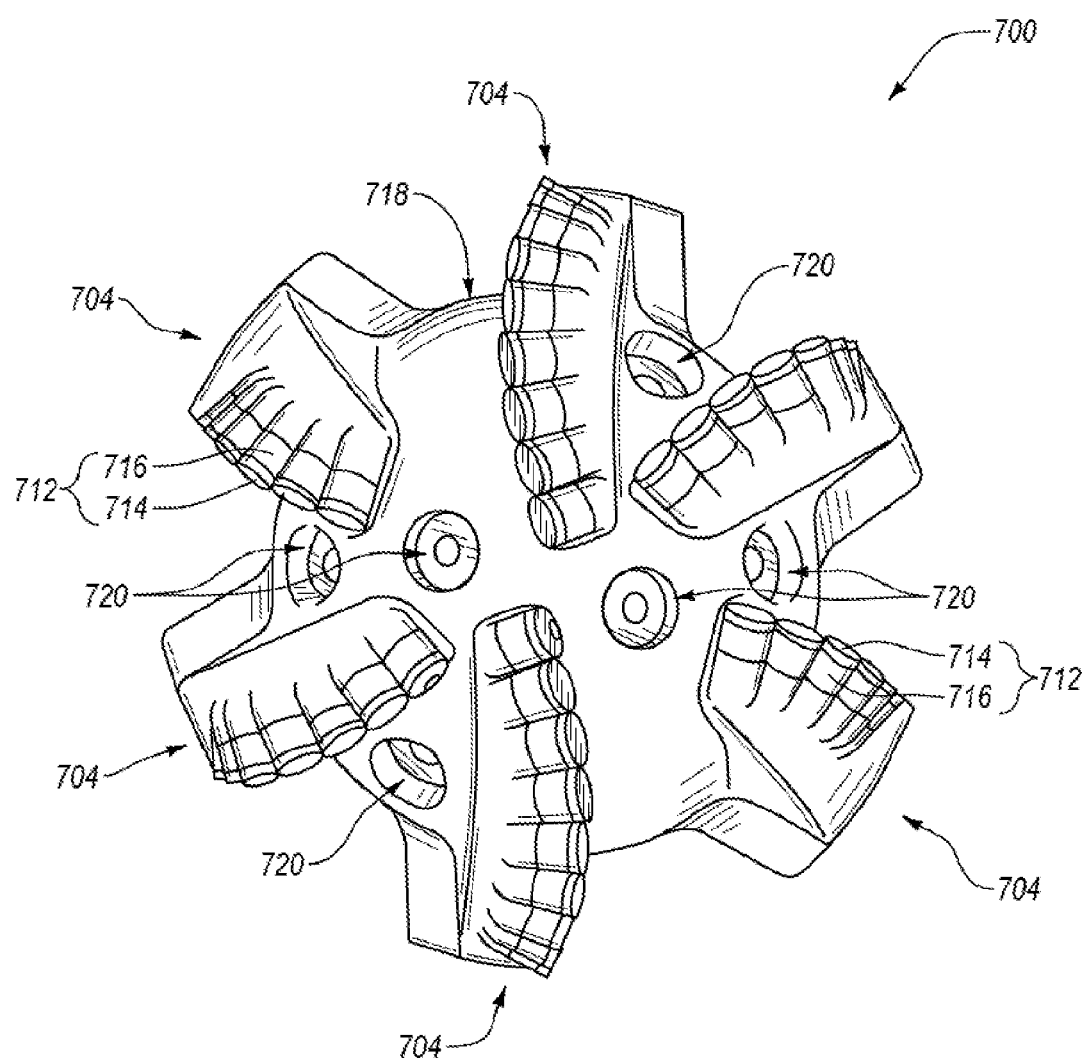
FIG. 8 is a top elevation view of the rotary drill bit shown in FIG. 7.

FIG. 7 is an isometric view and FIG. 8 is a top elevation view of a rotary drill bit 700 according to an embodiment. The rotary drill bit 700 includes at least one PDC cutting element configured according to any of the previously described leached PDC embodiments. The rotary drill bit 700 comprises a bit body 702 that includes radially and longitudinally extending blades 704 with leading faces 706, and a threaded pin connection 708 for connecting the bit body 702 to a drilling string. The bit body 702 defines a leading end structure configured for drilling into a subterranean formation by rotation about a longitudinal axis 710 and application of weight-on-bit. At least one PDC cutting element, manufactured and configured according to any of the previously described leached PDC embodiments, may be affixed to rotary drill bit 700 by, for example, brazing, mechanical affixing, or another suitable technique. With reference to FIG. 8, each of a plurality of PDCs 712 is secured to the blades 704. For example, each PDC 712 may include a PCD table 714 bonded to a substrate 716. More generally, the PDCs 712 may comprise any PDC disclosed herein, without limitation. In addition, if desired, in an embodiment, a number of the PDCs 712 may be conventional in construction. Also, circumferentially adjacent blades 704 define so-called junk slots 718 therebetween, as known in the art. Additionally, the rotary drill bit 700 includes a plurality of nozzle cavities 720 for communicating drilling fluid from the interior of the rotary drill bit 700 to the PDCs 712.

FIGS. 7 and 8 merely depict one embodiment of a rotary drill bit that employs at least one cutting element comprising a leached PDC fabricated and structured in accordance with the disclosed embodiments, without limitation. The rotary drill bit 700 is used to represent any number of earth-boring tools or drilling tools, including, for example, core bits, roller-cone bits, fixed-cutter bits, eccentric bits, bicenter bits, reamers, reamer wings, mining rotary drill bits, or any other downhole tool including PDCs, without limitation.

The leached PDCs disclosed herein may also be utilized in applications other than rotary drill bits. For example, the disclosed leached PDC embodiments may be used in thrust-bearing assemblies, radial bearing assemblies, wire-drawing dies, artificial joints, machining elements, PCD windows, and heat sinks.

Figure 9:
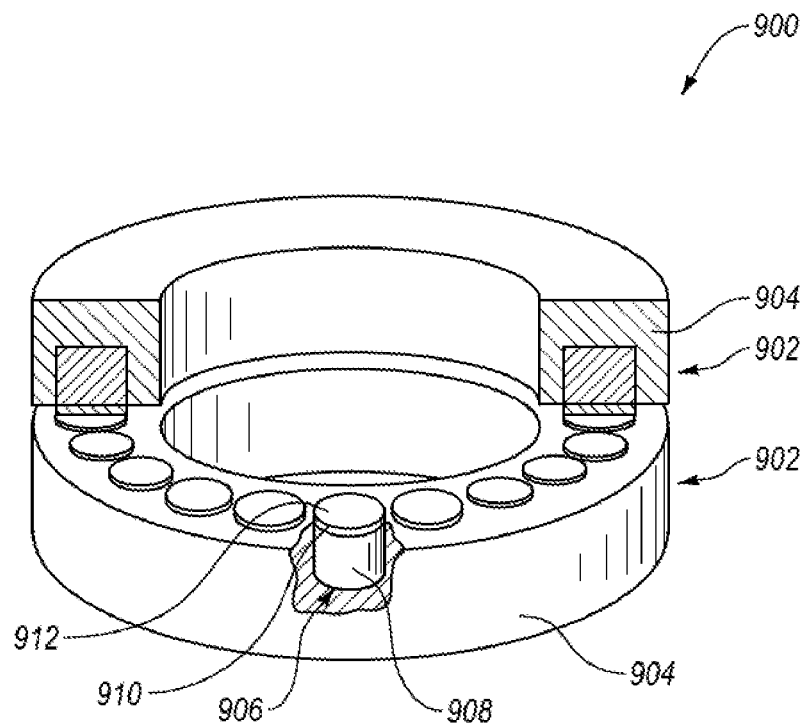
FIG. 9 is an isometric cutaway view of a thrust-bearing apparatus according to an embodiment, which may utilize any of the disclosed leached PDCs disclosed herein as bearing elements.

FIG. 9 is an isometric cutaway view of a thrust-bearing apparatus 900 according to an embodiment, which may utilize any of the disclosed leached PDC embodiments as bearing elements. The thrust-bearing apparatus 900 includes respective thrust-bearing assemblies 902. Each thrust-bearing assembly 902 includes an annular support ring 904 that may be fabricated from a material, such as carbon steel, stainless steel, or another suitable material. Each support ring 904 includes a plurality of recesses (not labeled) that receives a corresponding bearing element 906. Each bearing element 906 may be mounted to a corresponding support ring 904 within a corresponding recess by brazing, press-fitting, using fasteners, or another suitable mounting technique. One or more, or all of bearing elements 906 may be manufactured and configured according to any of the disclosed leached PDC embodiments. For example, each bearing element 906 may include a substrate 908 and a PCD table 910, with the PCD table 910 including a bearing surface 912.

In use, the bearing surfaces 912 of one of the thrust-bearing assemblies 902 bears against the opposing bearing surfaces 912 of the other one of the bearing assemblies 902. For example, one of the thrust-bearing assemblies 902 may be operably coupled to a shaft to rotate therewith and may be termed a "rotor." The other one of the thrust-bearing assemblies 902 may be held stationary and may be termed a "stator."

Figure 10:
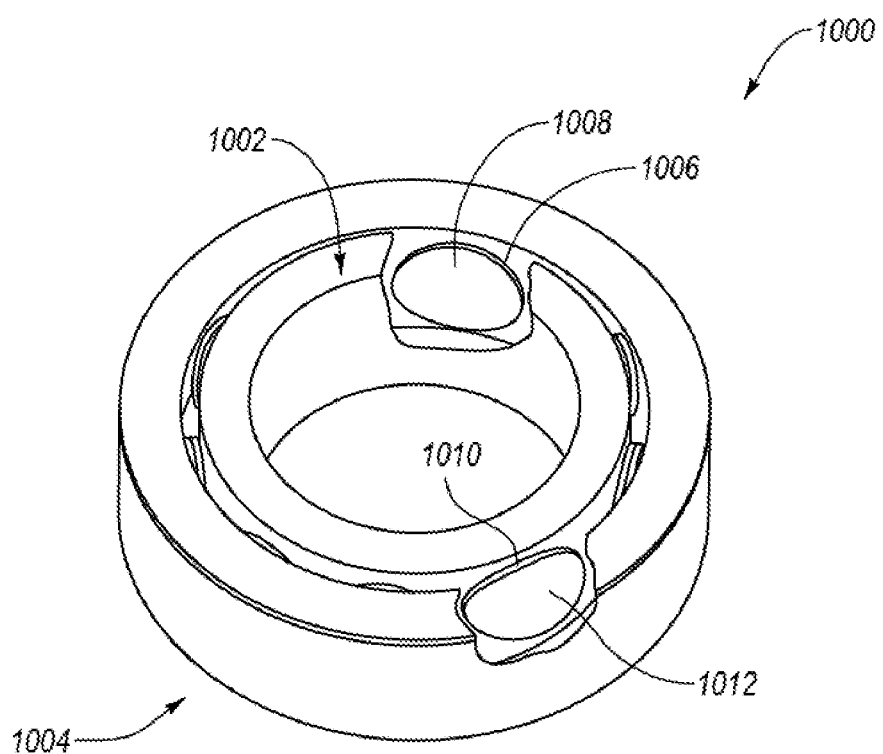
FIG. 10 is an isometric cutaway view of a radial bearing apparatus according to an embodiment, which may utilize any of the leached PDCs disclosed herein as bearing elements.

FIG. 10 is an isometric cutaway view of a radial bearing apparatus 1000 according to an embodiment, which may utilize any of the disclosed leached PDC embodiments as bearing elements. The radial bearing apparatus 1000 includes an inner race 1002 positioned generally within an outer race 1004. The outer race 1004 includes a plurality of bearing elements 1006 affixed thereto that have respective bearing surfaces 1008. The inner race 1002 also includes a plurality of bearing elements 1010 affixed thereto that have respective bearing surfaces 1012. One or more, or all of the bearing elements 1006 and 1010 may be configured according to any of the leached PDC embodiments disclosed herein. The inner race 1002 is positioned generally within the outer race 1004, with the inner race 1002 and outer race 1004 configured so that the bearing surfaces 1008 and 1012 may at least partially contact one another and move relative to each other as the inner race 1002 and outer race 1004 rotate relative to each other during use.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A method of leaching polycrystalline diamond, comprising:
    providing a polycrystalline diamond table including a plurality of bonded diamond grains defining a plurality of interstitial regions in which a metallic material is disposed;
    positioning the polycrystalline diamond table in contact with a leaching agent to at least partially remove the metallic material from the polycrystalline diamond table;
    periodically or substantially continuously measuring a concentration of at least one constituent of the leaching agent during the act of leaching;
    determining a leach depth of the polycrystalline diamond table at least partially based on the measured concentration of the at least one constituent of the leaching agent; and
    leaching the polycrystalline diamond table to a selected depth at least partially based on the measured concentration of the at least one constituent of the leaching agent.

2. The method of claim 1 wherein measuring a concentration of at least one constituent of the leaching agent includes periodically measuring the concentration.

3. The method of claim 1 wherein periodically or substantially continuously measuring a concentration of at least one constituent of the leaching agent includes substantially continuously measuring the concentration in situ during the act of leaching.

4. The method of claim 1 wherein measuring a concentration of at least one constituent of the leaching agent includes measuring the concentration with a spectrometer configured to provide substantially continuous measurement of the concentration of the at least one metal in the leaching agent.

5. The method of claim 1 wherein measuring a concentration of at least one constituent of the leaching agent includes measuring the concentration by at least one of inductively coupled plasma spectroscopy, inductively coupled plasma atomic mass spectrometry, or inductively coupled plasma emission spectroscopy.

6. The method of claim 1 wherein measuring a concentration of at least one constituent of the leaching agent includes:
    removing a sample of the leaching agent; and
    measuring the concentration of the at least one metal in the sample.

7. The method of claim 1 wherein measuring a concentration of at least one constituent of the leaching agent includes measuring the concentration at least once every about 2 hours for about 24 hours.

8. The method of claim 1 wherein measuring a concentration of at least one constituent of the leaching agent includes measuring the concentration at least once every about 4 hours for about 24 hours.

9. The method of claim 1 wherein measuring a concentration of at least one constituent of the leaching agent includes measuring the concentration over a period of up to about 7 days.

10. The method of claim 1 wherein the leach depth is less than about 1000 µm.

11. The method of claim 1 wherein the leach depth is about 50 µm to about 100 µm.

12. The method of claim 1 wherein the at least one constituent includes the metallic material.

13. The method of claim 1 wherein the metallic material includes at least one of a metal-solvent catalyst or a metallic infiltrant.

14. The method of claim 1 wherein the polycrystalline diamond table is bonded to a substrate prior to the act of leaching.

15. A method of modeling leaching behavior, comprising:
    providing a first polycrystalline diamond table including a first plurality of bonded diamond grains defining a plurality of interstitial regions in which a metallic material is disposed;
    positioning the first polycrystalline diamond table in contact with a first leaching agent to at least partially remove the metallic material from the polycrystalline diamond table;
    analyzing the first leaching agent to determine a concentration of at least one metal from the metallic material present in the leaching agent at selected time intervals;
    determining a leach depth of the first polycrystalline diamond table at each of the selected time intervals;
    correlating the determined leach depth and the determined concentration at each of the corresponding ones of the selected time intervals to generate a model of leaching behavior for the polycrystalline diamond table;
    positioning a second polycrystalline diamond table at least partially in a second leaching agent;
    determining a leach depth of the second diamond table at least partially based on the model of leaching behavior; and
    leaching the second polycrystalline diamond table to a selected depth at least partially based on the determined leach depth.

16. The method of claim 15 wherein the selected time intervals are at least once every about 4 hours for about 24 hours.

17. The method of claim 15 wherein the selected time intervals are at least once every about 4 hours for about 24 hours, followed by once about every 24 hours for a period of up to about 7 days.

18. The method of claim 15 wherein the leach depth is less than about 1000 µm.

19. The method of claim 15 wherein the metallic material includes at least one of a metal-solvent catalyst or a metallic infiltrant.

20. The method of claim 15, wherein determining a leach depth of the first polycrystalline diamond table includes exposing the polycrystalline diamond table to radiation.

21. A method of monitoring leaching, comprising:
    positioning a polycrystalline diamond table in a leaching agent to at least partially remove metallic material from the polycrystalline diamond table, wherein the polycrystalline diamond table includes a plurality of bonded diamond grains defining a plurality of interstitial regions in which the metallic material is disposed;

measuring a concentration of at least one constituent of the leaching agent;

predicting a leach depth in the polycrystalline diamond table at least partially based on the measured concentration; and leaching the polycrystalline diamond table to a selected depth at least partially based on the predicted leach depth.

22. The method of claim 21 wherein measuring a concentration of the at least one constituent of the leaching agent includes periodically measuring the concentration.

23. The method of claim 21 wherein measuring a concentration of at least one constituent of the leaching agent includes substantially continuously measuring the concentration in situ during the act of leaching.

24. The method of claim 21 wherein measuring a concentration of at least one constituent of the leaching agent includes measuring the concentration by at least one technique selected from the group consisting of inductively coupled plasma spectroscopy, inductively coupled plasma atomic mass spectrometry, and inductively coupled plasma emission spectroscopy.

25. The method of claim 21, further comprising modifying the leaching process responsive to the act of predicting.

26. The method of claim 21 wherein the metallic material includes at least one of a metal-solvent catalyst or a metallic infiltrant.

* * * * *